(12) United States Patent
Keady

(10) Patent No.: US 11,291,456 B2
(45) Date of Patent: Apr. 5, 2022

(54) EXPANDABLE SEALING DEVICES AND METHODS

(71) Applicant: Staton Techiya LLC, Delray Beach, FL (US)

(72) Inventor: John P Keady, Fairfax Station, VA (US)

(73) Assignee: Staton Techiya, LLC, Delray Beach, FL (US)

( * ) Notice: Subject to any disclaimer, the term of this patent is extended or adjusted under 35 U.S.C. 154(b) by 0 days.

(21) Appl. No.: 16/851,896

(22) Filed: Apr. 17, 2020

(65) Prior Publication Data

US 2020/0237377 A1  Jul. 30, 2020

Related U.S. Application Data

(63) Continuation-in-part of application No. 14/176,184, filed on Feb. 10, 2014, now abandoned, which is a continuation of application No. 12/172,834, filed on Jul. 14, 2008, now Pat. No. 8,678,011.

(60) Provisional application No. 60/949,398, filed on Jul. 12, 2007.

(51) Int. Cl.
| | |
|---|---|
| *A61F 11/10* | (2006.01) |
| *H04R 1/10* | (2006.01) |
| *A61B 17/12* | (2006.01) |
| *A61F 5/00* | (2006.01) |
| *H04R 25/00* | (2006.01) |

(52) U.S. Cl.
CPC .. *A61B 17/12136* (2013.01); *A61B 17/12104* (2013.01); *A61B 17/12109* (2013.01); *A61F 5/0093* (2013.01); *A61F 11/10* (2013.01); *H04R 1/1016* (2013.01); *H04R 25/652* (2013.01); *H04R 25/658* (2013.01)

(58) Field of Classification Search
CPC ...... A61F 11/10; A61F 5/0093; A61F 11/008; A61F 11/08; A61F 2011/085; H04R 1/1016; H04R 25/652; H04R 25/658; A61B 17/12104; A61B 17/12109; A61B 17/12136
See application file for complete search history.

(56) References Cited

U.S. PATENT DOCUMENTS

| | | | |
|---|---|---|---|
| 2,493,326 | A | 1/1950 | Trinder |
| 2,535,258 | A | 12/1950 | Bland |
| 2,876,767 | A | 3/1955 | Wasserman |
| 3,505,999 | A | 4/1970 | Harvey et al. |
| 3,602,654 | A | 8/1971 | Victoreen |
| 4,020,297 | A | 4/1977 | Brodie |
| 4,060,080 | A | 11/1977 | Akiyama |
| 4,133,984 | A | 1/1979 | Akiyama |
| 4,160,449 | A | 7/1979 | Wade |
| 4,392,858 | A | 7/1983 | George et al. |
| 4,539,440 | A | 9/1985 | Sciarra |
| 4,582,053 | A | 4/1986 | Wilson |
| 4,741,344 | A | 5/1988 | Danby et al. |

(Continued)

FOREIGN PATENT DOCUMENTS

CN   107071123   8/2017

*Primary Examiner* — Camtu T Nguyen
(74) *Attorney, Agent, or Firm* — Akerman LLP; Peter A. Chiabotti

(57) ABSTRACT

An insertion device includes a stent and a plurality of sealing elements where each sealing element is operatively attached to the stent and an earclip retention system.

18 Claims, 10 Drawing Sheets

(56) References Cited

U.S. PATENT DOCUMENTS

| | | | |
|---|---|---|---|
| 4,834,211 A | 5/1989 | Bibby | |
| 4,896,679 A | 1/1990 | St. Pierre | |
| 4,962,537 A | 10/1990 | Basel et al. | |
| 5,033,090 A | 7/1991 | Weinrich | |
| 5,138,722 A | 8/1992 | Urella | |
| 5,142,587 A | 8/1992 | Kobayashi | |
| 5,319,163 A | 6/1994 | Scott | |
| 5,333,622 A | 8/1994 | Casali et al. | |
| 5,483,027 A | 1/1996 | Krause | |
| 5,712,453 A | 1/1998 | Bungardt | |
| 5,764,781 A | 6/1998 | Ding | |
| 6,094,494 A | 7/2000 | Haroldson | |
| 6,256,396 B1 | 7/2001 | Cushman | |
| 6,321,070 B1 | 11/2001 | Clark | |
| 6,339,648 B1 | 1/2002 | Mcintosh et al. | |
| 6,393,130 B1 | 5/2002 | Stonikas et al. | |
| 6,513,621 B1 | 2/2003 | Deslauriers et al. | |
| 6,607,546 B1 | 8/2003 | Murken | |
| 6,671,381 B1 | 12/2003 | Lux-Wellenhof | |
| 6,768,804 B1 * | 7/2004 | Isvan | H04R 1/083 181/20 |
| 7,130,437 B2 | 10/2006 | Stonikas et al. | |
| 7,164,775 B2 | 1/2007 | Meyer et al. | |
| 7,227,968 B2 | 9/2007 | Zeger van Halteren et al. | |
| 7,362,875 B2 | 4/2008 | Saxton et al. | |
| 7,387,187 B2 | 6/2008 | Widmer et al. | |
| 7,688,983 B2 | 3/2010 | Voix | |
| 7,756,281 B2 | 7/2010 | Goldstein et al. | |
| 7,801,318 B2 | 9/2010 | Barthel | |
| 8,047,207 B2 | 11/2011 | Perez et al. | |
| 8,194,864 B2 | 6/2012 | Goldstein et al. | |
| 8,199,919 B2 | 6/2012 | Goldstein et al. | |
| 8,208,644 B2 | 6/2012 | Goldstein et al. | |
| 8,208,652 B2 | 6/2012 | Keady | |
| 8,221,861 B2 | 7/2012 | Keady | |
| 8,229,128 B2 | 7/2012 | Keady | |
| 8,251,925 B2 | 8/2012 | Keady et al. | |
| 8,312,960 B2 | 11/2012 | Keady | |
| 8,401,200 B2 | 3/2013 | Tiscareno | |
| 8,437,492 B2 | 5/2013 | Goldstein et al. | |
| 8,550,206 B2 | 10/2013 | Keady | |
| 8,554,350 B2 | 10/2013 | Keady et al. | |
| 8,600,067 B2 | 12/2013 | Usher et al. | |
| 8,631,801 B2 | 1/2014 | Keady | |
| 8,657,064 B2 | 2/2014 | Staab et al. | |
| 8,678,011 B2 | 3/2014 | Goldstein et al. | |
| 8,718,313 B2 | 5/2014 | Keady | |
| 8,774,433 B2 | 7/2014 | Goldstein | |
| 8,774,435 B2 | 7/2014 | Ambrose | |
| 8,848,939 B2 | 9/2014 | Keady et al. | |
| 8,917,880 B2 | 12/2014 | Goldstein et al. | |
| 8,992,710 B2 | 3/2015 | Keady | |
| 9,084,060 B2 | 7/2015 | Liu | |
| 9,113,267 B2 | 8/2015 | Usher et al. | |
| 9,123,323 B2 | 9/2015 | Keady | |
| 9,138,353 B2 | 9/2015 | Keady | |
| 9,185,481 B2 | 11/2015 | Goldstein et al. | |
| 9,216,237 B2 | 12/2015 | Keady | |
| 9,293,128 B2 | 3/2016 | Goldstein | |
| 9,539,147 B2 | 1/2017 | Keady et al. | |
| 9,757,069 B2 | 9/2017 | Keady et al. | |
| 9,781,530 B2 | 10/2017 | Usher et al. | |
| 9,814,625 B2 * | 11/2017 | Ely | A61F 11/12 |
| 9,843,854 B2 | 12/2017 | Keady | |
| 10,012,529 B2 | 7/2018 | Goldstein et al. | |
| 10,190,904 B2 | 1/2019 | Goldstein et al. | |
| 2004/0215053 A1 | 10/2004 | Jorgensen et al. | |
| 2004/0258263 A1 | 12/2004 | Saxton et al. | |
| 2005/0054988 A1 | 3/2005 | Rosenberg et al. | |
| 2005/0058313 A1 | 3/2005 | Victorian et al. | |
| 2005/0075662 A1 | 4/2005 | Pedersen et al. | |
| 2006/0025653 A1 | 2/2006 | Bachler | |
| 2006/0159298 A1 | 7/2006 | von Dombrowski et al. | |
| 2006/0175722 A1 | 8/2006 | Babcock et al. | |
| 2007/0083217 A1 | 4/2007 | Eversull et al. | |
| 2007/0116319 A1 | 5/2007 | Hagberg | |
| 2008/0144871 A1 | 6/2008 | Purcell et al. | |
| 2009/0071487 A1 | 3/2009 | Keady | |
| 2009/0173353 A1 | 7/2009 | Purcell et al. | |
| 2009/0320858 A1 | 12/2009 | Purcell et al. | |
| 2009/0320859 A1 | 12/2009 | Purcell et al. | |
| 2010/0241256 A1 | 9/2010 | Goldstein et al. | |
| 2013/0098706 A1 | 4/2013 | Keady | |
| 2013/0149192 A1 | 6/2013 | Keady | |
| 2013/0177179 A1 | 7/2013 | Ambrose | |
| 2014/0003644 A1 | 1/2014 | Keady et al. | |
| 2014/0026665 A1 | 1/2014 | Keady | |
| 2014/0247948 A1 | 9/2014 | Goldstein | |
| 2014/0247952 A1 | 9/2014 | Goldstein | |
| 2014/0373854 A1 | 12/2014 | Keady | |
| 2016/0015568 A1 | 1/2016 | Keady | |
| 2016/0192077 A1 | 6/2016 | Keady | |
| 2016/0295311 A1 | 10/2016 | Keady et al. | |
| 2017/134865 A1 | 5/2017 | Goldstein et al. | |
| 2018/0054668 A1 | 2/2018 | Keady | |
| 2018/0132048 A1 | 5/2018 | Usher et al. | |
| 2018/0176681 A1 | 6/2018 | Asada | |
| 2018/0220239 A1 | 8/2018 | Keady et al. | |
| 2019/0082272 A9 | 3/2019 | Goldstein et al. | |

* cited by examiner

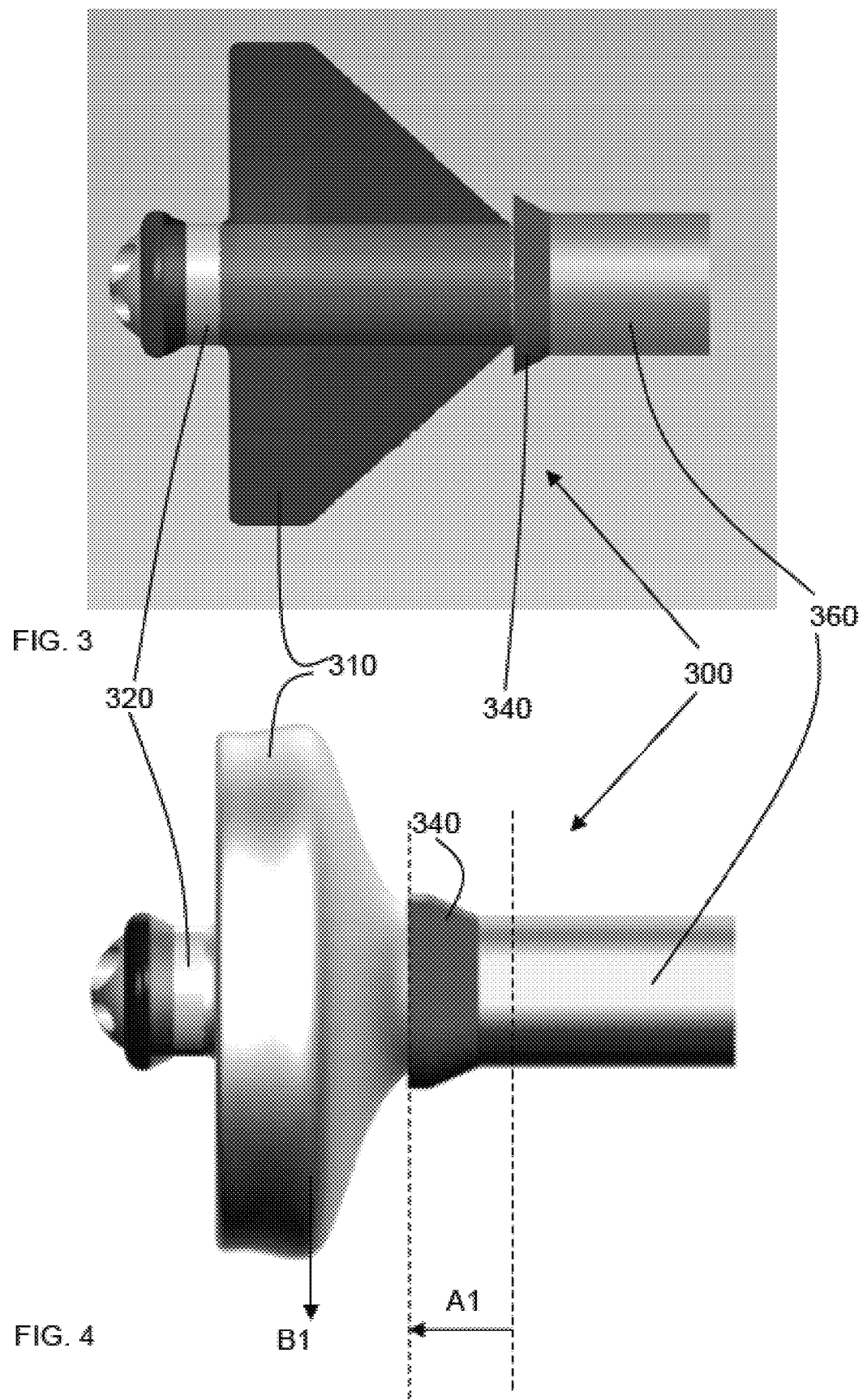

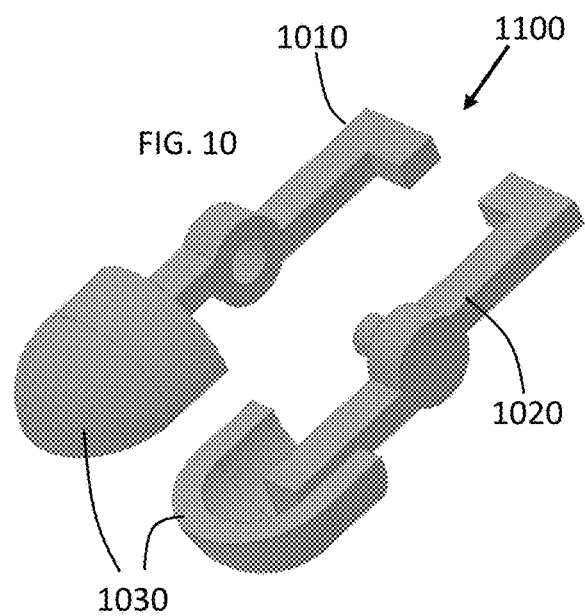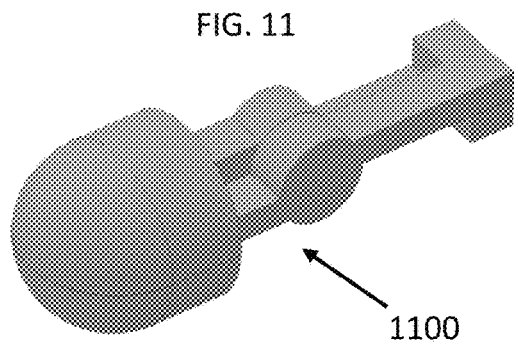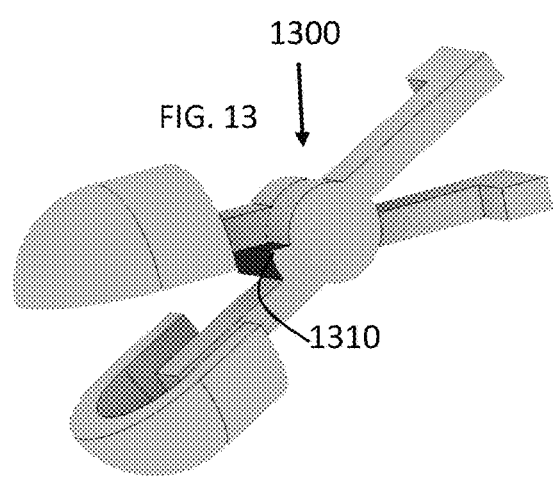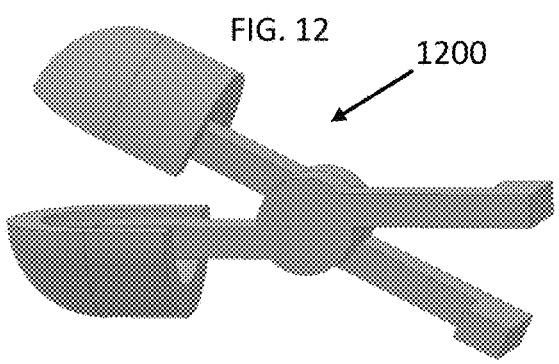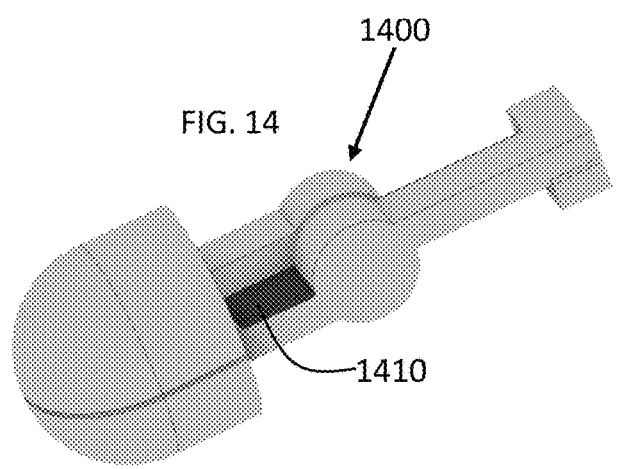

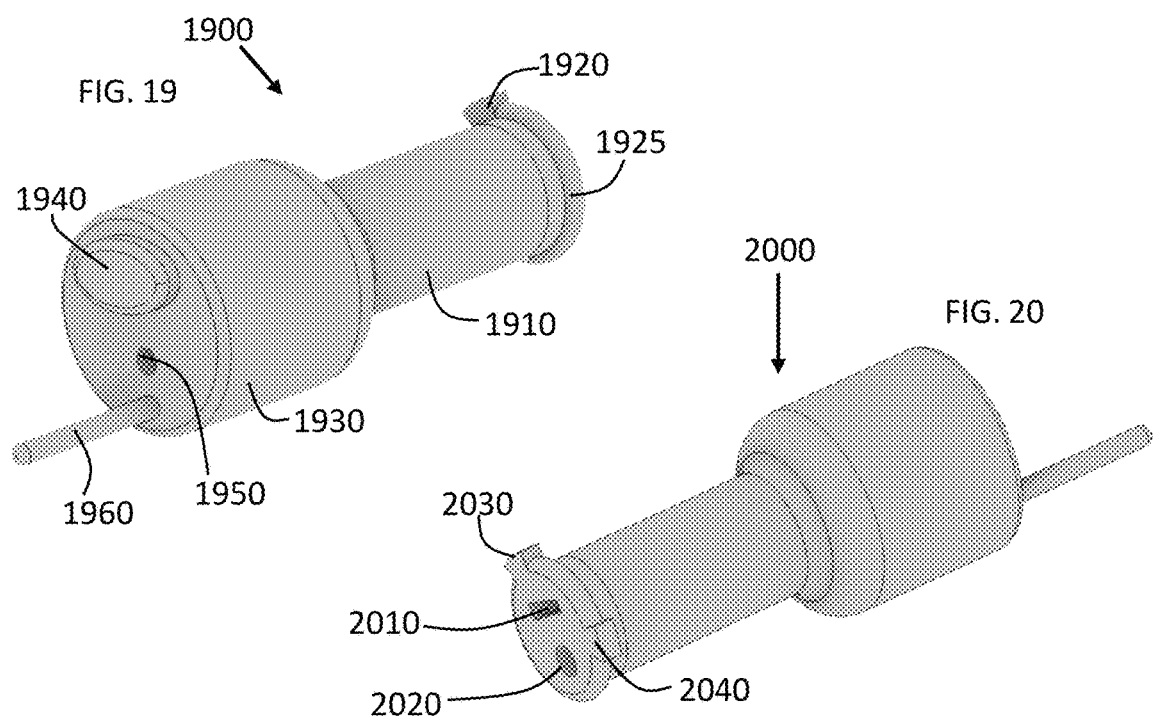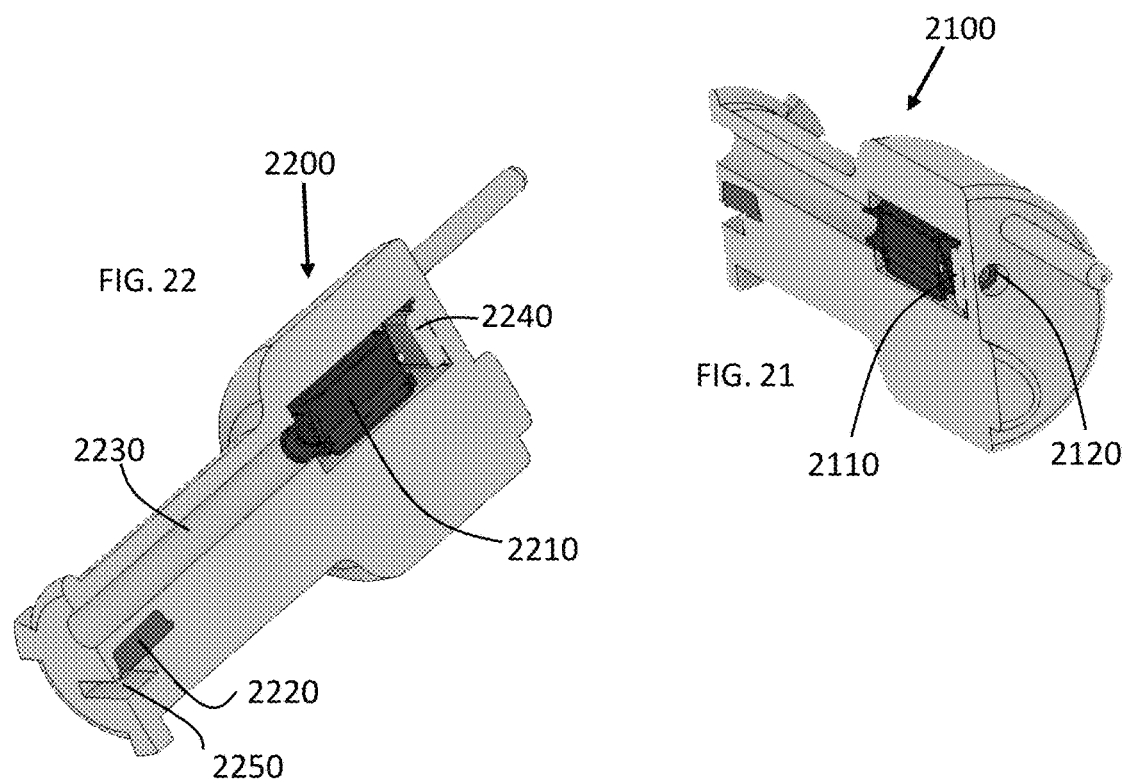

EXPANDABLE SEALING DEVICES AND METHODS

CROSS REFERENCE TO RELATED APPLICATIONS

This Application is a Continuation in Part of and claims priority to U.S. patent application Ser. No. 14/176,184 filed 10 Feb. 2014, which is a Continuation of and claims the priority benefit of U.S. patent application Ser. No. 12/172,834 filed on 14 Jul. 2008 which claims the priority benefit of Provisional Application No. 60/949,398 filed on 12 Jul. 2007, the entire disclosure of all of which are incorporated herein by reference in their entirety.

FIELD

The invention relates in general to devices and methods of earphone, earpiece, earbud or orifice, fit and sealing technology, and particularly though not exclusively, is related to expandable sealing mechanisms for earphones.

BACKGROUND

Present day ear devices are intended to deliver information to the ear via off-the-shelf or custom-molded pieces that present the information primarily in the outer third of the ear canal, often with questionable attention to the actual fit, comfort, and consideration of the ear anatomy and physiology.

FIG. 1A illustrates a generic cross section of an ear canal 5100, including a cartilaginous region 5140 and a bony region 5130 of an ear canal 5120. The entrance of the ear canal 5120 is referred to as the aperture 5150 and defines a first end of the ear canal while the tympanic membrane 5110 defines the other end of the ear canal 5120.

FIG. 2A illustrates general outer physiology of an ear, which includes a, auricle tubercle 6210, the antihelix 6220, the helix 6230, the antitragus 6240, tragus 6250, lobule of ear 6260, crus of helix 6270, anterior notch 6280, and intertragic incisures 6290.

Current systems do not use inflatable or expandable systems to achieve sound isolation and sealing.

SUMMARY

At least one exemplary embodiment is related to an earpiece (e.g., earphone, earbud, or other devices configured to direct acoustic signals to the ear) inserted into the ear canal, where a portion of a sealant section acoustically seals a medial portion of the external auditory canal.

At least one exemplary embodiment is directed to an earpiece that includes: a sealing section, where the sealing section includes an expandable bladder; an ambient sound microphone (ASM); an ear canal receiver (ECR); an ear canal microphone (ECM); a wireless communication module; a power source; and a logic circuit.

Further areas of applicability of embodiments will become apparent from the detailed description provided hereinafter. It should be understood that the detailed description and specific examples, while indicating exemplary embodiments, are intended for purposes of illustration only and are not intended to limit the scope of the embodiments.

BRIEF DESCRIPTION OF THE DRAWINGS

Exemplary embodiments of the present invention will become apparent from the following detailed description taken in conjunction with the following drawings, wherein:

FIGS. 3 and 4 illustrate a stent used to inflate an expandable section of the device;

FIG. 10 illustrates an example of an earclip support configuration, with a tip system included;

FIG. 11 illustrates an example of an earclip configuration;

FIG. 12 illustrates an example of an earclip configuration in a normal orientation;

FIG. 13 illustrates an example of an earclip configuration in a normal orientation with a retention system;

FIG. 14 illustrates an example of an earclip configuration in an insertion orientation;

FIG. 19 illustrates an example of an earphone configuration;

FIG. 20 illustrates an example of an earphone configuration of FIG. 19 from another view;

FIG. 21 illustrates an example of an cross sectional cut of the earphone configuration of FIG. 19 from a first view;

FIG. 22 illustrates an example of an cross sectional cut of the earphone configuration of FIG. 19 from a second view;

DETAILED DESCRIPTION

Figure 1:
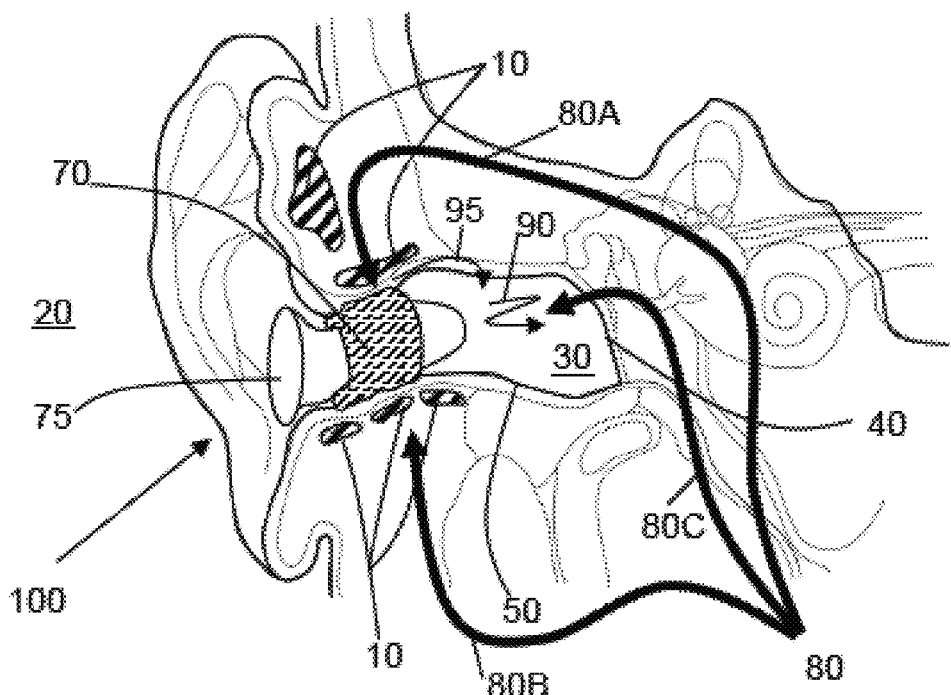
FIG. 1 illustrates an ear canal as a non-limiting example of an orifice that can be sealed with an orifice insertion device such as an earpiece according to at least one exemplary embodiment.

The following description of exemplary embodiment(s) is merely illustrative in nature and is in no way intended to limit the invention, its application, or uses.

Exemplary embodiments are directed to or can be operatively used on various wired or wireless orifice insertion devices such as earpiece devices (e.g., earbuds, headphones, ear terminals, hearing aids, behind the ear devices, or other acoustic devices as known by one of ordinary skill in the art, and equivalents).

Processes, techniques, apparatus, and materials as known by one of ordinary skill in the art may not be discussed in detail but are intended to be part of the enabling description where appropriate. For example material fabrication methods may not be disclosed, nor attachment procedures (e.g., adhesive attaching of separate ridge structures), but such, as known by one of ordinary skill in such arts is intended to be included in the discussion herein when necessary.

Notice that similar reference numerals and letters refer to similar items in the following figures, and thus once an item is defined in one figure, it may not be discussed or further defined in the following figures. Note also that all examples discussed herein are non-limiting and not meant to limit function or form of any invention claimed herein.

FIG. 1 illustrates a sealed (occluded) ear canal 50, with a sealed volume 30 (sealed from receiving sound from ambient environment 20). Voice can leak 80 into the sealed volume 30 between insertion element 75 and eardrum 40 from various source paths 80A, 80B, and 80C. Source paths 80A and 80B represent sound conducted from bones 10 adjacent to ear canal 50. Source path 80C represents sounds 90, 95 to ear canal 50 from other areas of the ear. In one explanation, the leaked acoustic energy results in an amplification (e.g., by resonance) at certain frequencies within the sealed volume, resulting in the occlusion effect. If the ear canal 50 (a non-limiting example of an orifice) was unsealed then no resonance could build and hence there would be no occlusion effect. While the present example has been described with reference to exemplary embodiments, it is to be understood that the embodiments herein not limited to the disclosed exemplary embodiments. The scope of the following claims is to be accorded the broadest interpretation so as to encompass all modifications, equivalent structures and functions of the relevant exemplary embodiments.

FIG. 1 illustrates at least one exemplary embodiment. An earpiece 100 can include an insertion element 75 operatively connected to a sealing section. The sealing section can include an expandable section 70 (e.g., expanding polymers, inflatable systems, mechanically expanded systems).

The expandable section 70 can be inflatable (e.g., fluid (gas or liquid)) of deformable tillable material. For example the tillable material referred to herein can be viscous and can include silicone-based polymers, gels, vinyl elastomers, or any other material of sufficient properties to allow the deformation of a membrane cavity from user contact. Materials can also be used to provide a slow reformation of the original membrane cavity shape after it has been deformed and released. In this regard, a silicone gel or other non-cross-linked polymer or uncatalyzed materials may be used. It should be appreciated that the composition of the tillable material could be altered for applications in which varied membrane characteristics are desired (i.e. more stiffness, durability, more or less deformability and/or longer-lasting deformation). The tillable material may be elastically deformed or it may be deformed by displacement, which is the actual movement or flow of the tillable material in response to pressure, such as that from a user's fingertips. In addition, the tillable material could be altered for applications in which varied temperature or light conditions would be encountered during the use of particular products on which the membrane cavity is mounted.

The portion of a membrane connected to a structure (base membrane) can be made of any material, rigid or elastic, including various plastic or metal materials, or it can be made of a membrane formed of thin rubber-based material, deformable plastic or silicone-based materials or other elastomeric materials suitable for a given application. If the base is configured as a flexible membrane, the cavity can more easily conform to a product's surface, thereby increasing the ease with which the cavity can be installed, removed, and replaced. Likewise, the outer membrane also can be made of a thin rubber-based material, deformable plastic or silicone polymer materials, or other elastomeric materials suitable for a given application. If the base membrane and outer membrane are made of silicone material, both should be from 0.50 mm to 2.5 mm in thickness. In this regard, the base may be a membrane instead of a piece of rigid material. The edges of the outer membrane and the base membrane can be mechanically fastened or clamped forming the membrane cavity. Additionally, at least a portion of the base membrane can be adhesively attached (e.g., adhesive tape, glue) or mechanically fastened to the support structure.

The silicone sealant can be of an acetoxy cure type. In particular, upon exposure to moisture, the silicone sealant will give off small amounts of acetic acid while the sealant cures. It is not recommended that the acetic acid vapors be inhaled. The sealant will cure in 24 hours and has a tack free time of 10-20 minutes at 77 degree. F. (25.degree.C.) with 50% relative humidity. The sealant's tensile strength is approximately 350 psi, its elongation property is 450%, and its hardness is approximately 25-30 Shore A. The sealant has temperature stability from −85.degree. F. to 450.degree. F. (−65.degree. C. to 232.degree. C.) and can withstand intermittent exposure to temperatures as high as 500.degree. F. (280.degree. C.). The sealant is believed to have good resistance to various weathering conditions, including UV radiation, rain, snow, etc, without hardening, cracking, or shrinking.

For optimum adhesion with the above adhesive, the support structure and the lower surface of the base membrane should be clean, dry, and free from oil, grease or other foreign material. If necessary, metal surfaces should be wiped with a non-oily solvent. Rubber surfaces should be abraded to promote adhesion. Depending on environmental conditions, the base and product surface should be joined within 5-10 minutes, before the tack-free time of the sealant passes.

If the expandable section 70 includes a fluid (gas or liquid) the fluid can be variable for example $H_2$, $O_2$, air, and water, where the membrane can be designed to vary porosity to the fluid leakage through the membrane. For example for some gases (e.g., $H_2$) the wall thickness can be increased (e.g., 3 times that of air) to decrease the porosity of $H_2$ through an inflatable membrane.

Typical dimensions of the expandable section include a fully expanded dimension that is slightly larger than the orifice (e.g., nose, throat, vein, anal, ear canal) opening.

Figure 2:
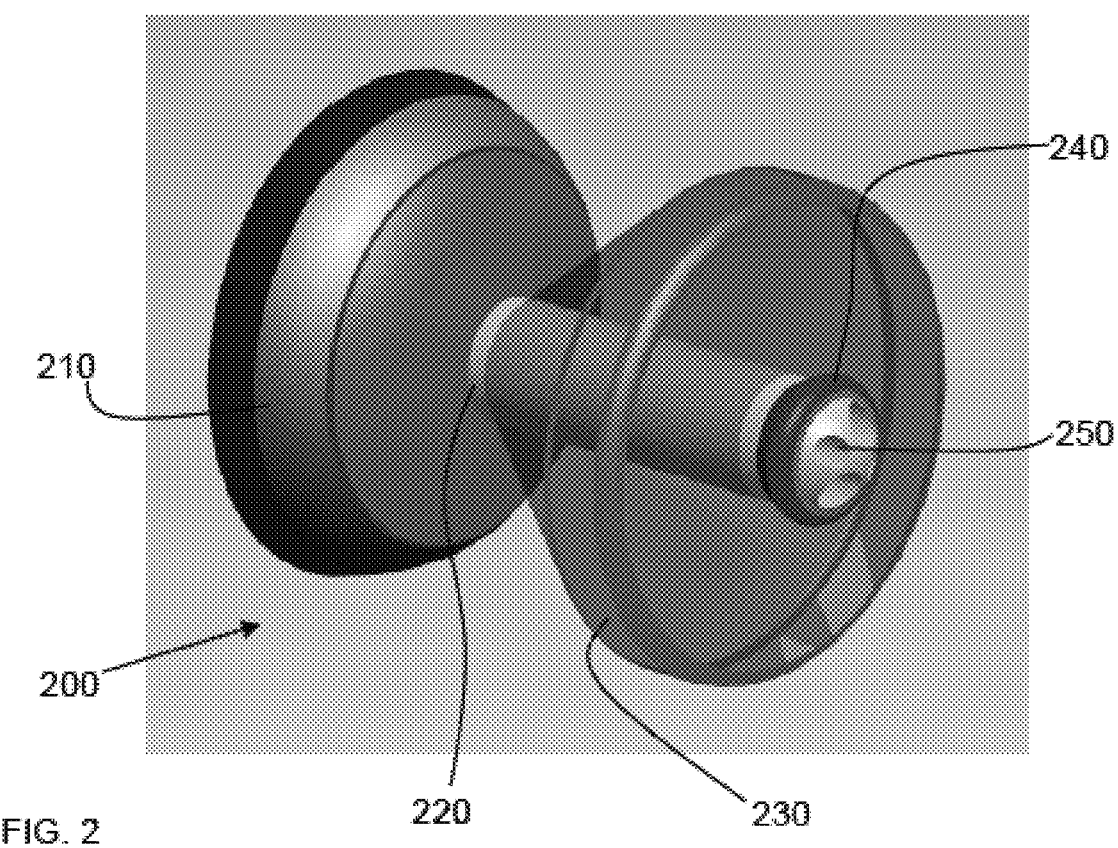
FIG. 2 illustrates an orifice insertion device according to at least one embodiment.
Figure 1A:
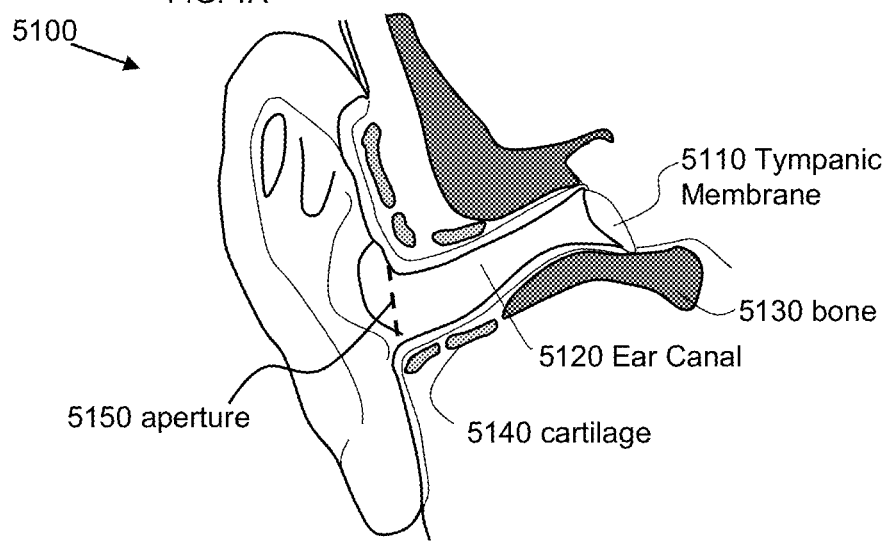
FIG. 1A illustrates a cartilaginous region and a bony region of an ear canal.
Figure 2A:
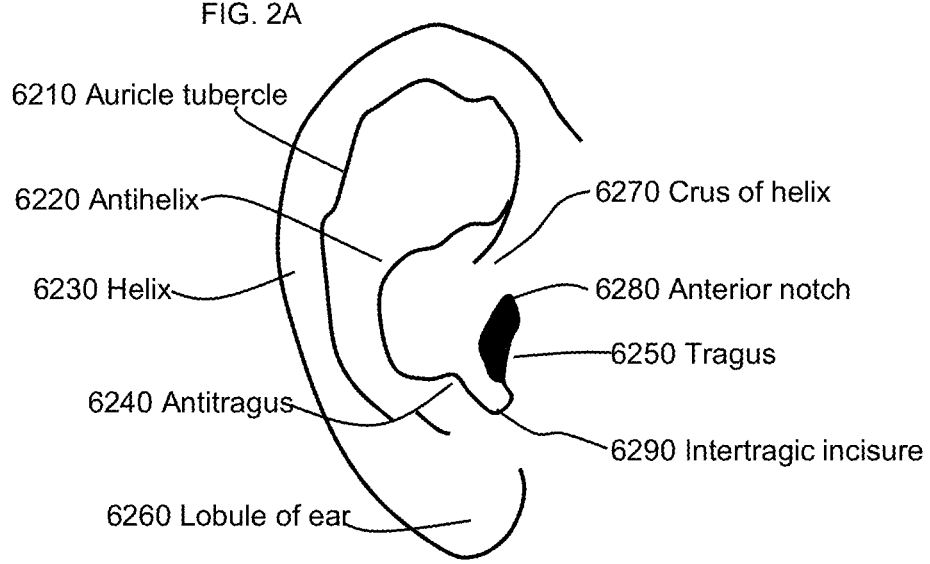
FIG. 2A illustrates general physiology of an ear.

FIG. 2 illustrates an orifice insertion device 200, that has an optional stop flange 210. The stop flange 210 can be designed to stop at the opening of an orifice. The stop flange 210 can be attached to a stent 220 (e.g., multilumen tube, single lumen tube) that can vary in durometer (e.g., 25-80 urethane, steel, wood). As illustrated in FIG. 2 the stent 220 is a multi-lumen tube with various openings (e.g., 250). An expandable section 230 can be operatively attached to the stent 220 (e.g., heat bonded, shrink wrapped, glued). Optionally a guide section 240 (e.g., soft foam tip, additional inflatable system) can be attached near the end of the stent 220 to aid in the insertion of the orifice device 200 (e.g., earpiece).

Figure 6:
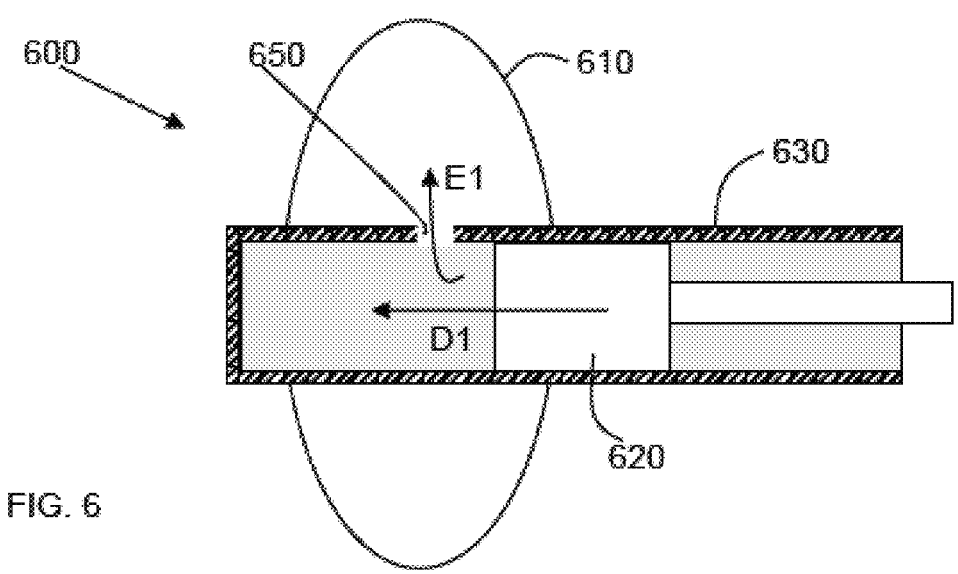
FIG. 6 illustrates an internal piston mechanism that can be used to increase the pressure in the inflatable membrane on a stent.

In an embodiment, the expandable section 230 of the earpiece is an inflatable device. Several methods can be used to inflate the expandable section 230. For example FIGS. 3 and 4 illustrate an orifice insertion device 300 including a stent 320, operatively connected to an inflatable membrane 310 (e.g., balloon), where a push mechanism (340 and 360) moves along the stent 320 in direction A1, to compress the inflatable membrane 310 along direction 81. Additionally FIG. 6 illustrates an orifice insertion device 600 including an internal piston mechanism 620 that can be used (e.g., moved along direction D1) to increase the pressure E1 in the inflatable membrane 610 on a stent 630 (via opening 650 in stent 630).

Figure 5:
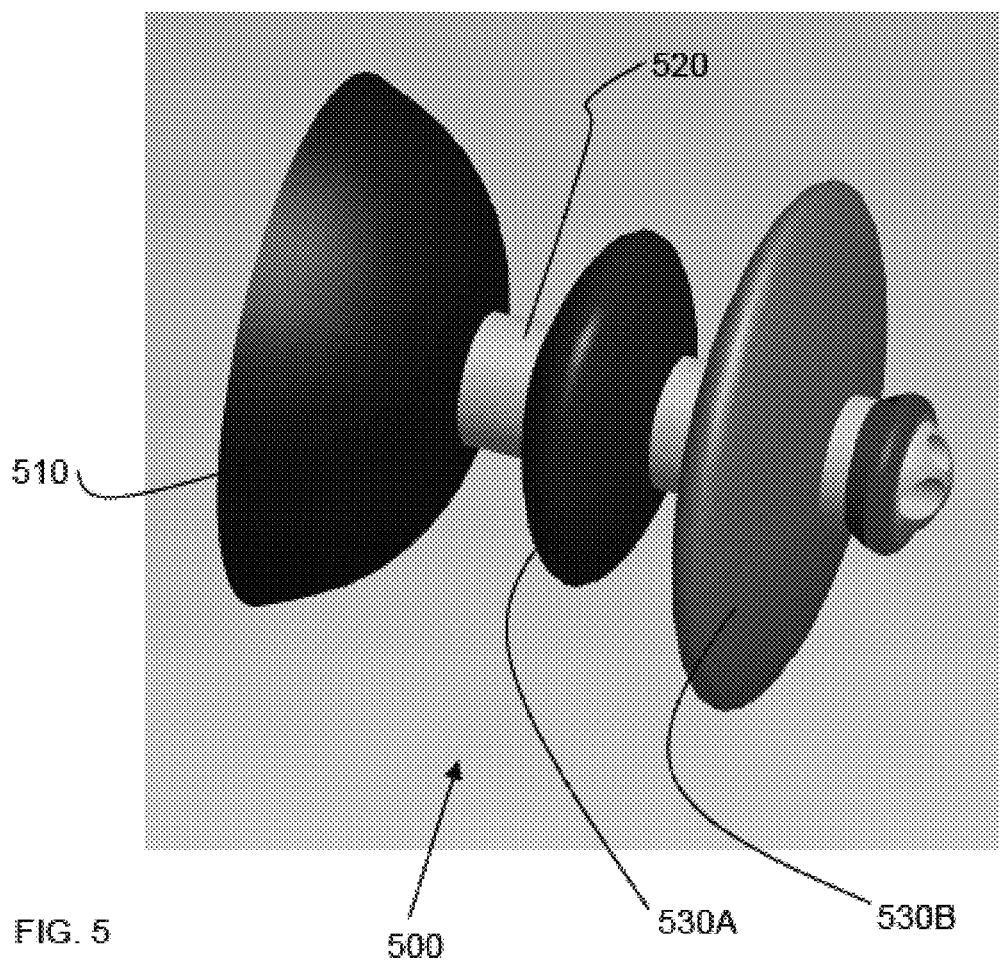
FIG. 5 illustrates a multiple expandable system where various combinations of expandable systems can be combined on a stent.

FIG. 5 illustrates a multiple expandable system where various combinations of expandable systems (e.g., one inflatable the other foam), can be combined on a stent 520. The orifice insertion device 500 illustrated in FIG. 5 shows two expandable section 530A and 5308. The orifice insertion device 500 also illustrates stop flange 510. Both can be expanded by methods discussed previously and at different times. For example expandable section 530A can be inflated (if it were an inflatable system) if a trigger event (e.g., excess sound pressure level (e.g., 100 dB)) were reached.

In the examples illustrated above the sealing sections have been illustrated as homogeneous material, which in some cases can expand in response to thermal variations. Additional exemplary embodiments can include expandable sections, that can include temperature expanding materials varying in a sandwich type configuration, and/or an expandable membrane or bladder that is expanded to touch and press against the ear canal wall to provide sealing. In addition to varying penetration into the depths of the ear canal for various devices, at least one exemplary embodiment includes an earpiece device that seals near the concha or the external auditory meatus. For example the earpiece device can have a concha support piece to which is attached to an ear terminal (portion penetrating into the ear canal), where the ear terminal seals and seats near the external auditory meatus.

In at least one exemplary embodiment the compression can be driven by a piston, where the piston can be driven by a linear actuator or via a pneumatic system where an incompressible fluid presses against one side of the piston forcing it in a direction compressing the bladder.

Additional exemplary embodiments can use an expandable bladder as a sealing section where one side of an inner wall moves as driven by actuators, gears, pneumatics or other methods as one of ordinary skill would know, and presses on the bladder expanding the bladder into the ear canal. The bladder can be attached to the moveable wall so that retraction of the wall retracts the bladder from the ear canal.

At least one exemplary embodiment is directed to an orifice insertion device comprising: a stent; and a sealing element where the sealing element is operatively attached to the stent, wherein the sealing element includes at least a first expandable section, where the expandable section is configured to exert a pressure on an orifice wall sufficient to seal the orifice without appreciable deformation of the orifice wall. The pressure exerted can vary depending upon the orifice wall's material composition and rigidity. For example in flesh the pressure exerted can lie between 1 atmospheres and 5 atmospheres, where an atmosphere is the pressure at sea level.

Note that herein many various materials can be used herein in the exemplary embodiments. For example 3D printing materials such as Formlabs™ tough resin, flexible resin can be used, rubber, silicone, and plastics.

Figure 7:
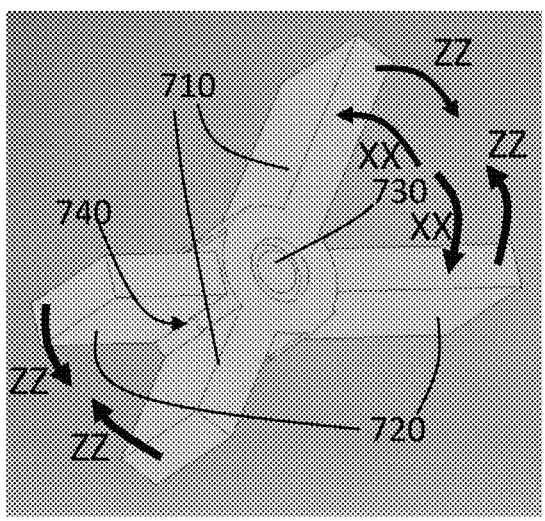
FIG. 7 illustrates an example of an earclip support configuration.

FIG. 7 illustrates an example of an earclip support configuration 700. The earclip support 700 consists of a first arm 710, a second arm 720, connected at a pivot 730. A resilient member can be added between the arms 710 and 720 to return the arms 710 and 720 to a set (referred to as normal) position, so that when the arms 710 and 720 are moved/actuated (ZZ) to an actuated state, then a resilient member placed at position 740 exerts a force returning (XX) the arm positions 710 and 720 to the "normal" pre-insertion position (state).

Figure 8:
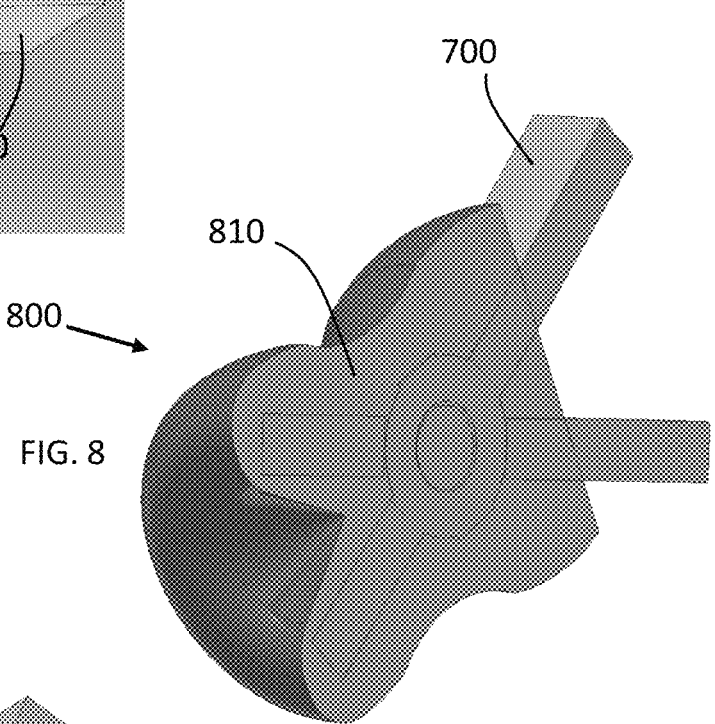
FIG. 8 illustrates a cut away of an example of an earclip earplug using the earclip support configuration shown in FIG. 7.
Figure 9:
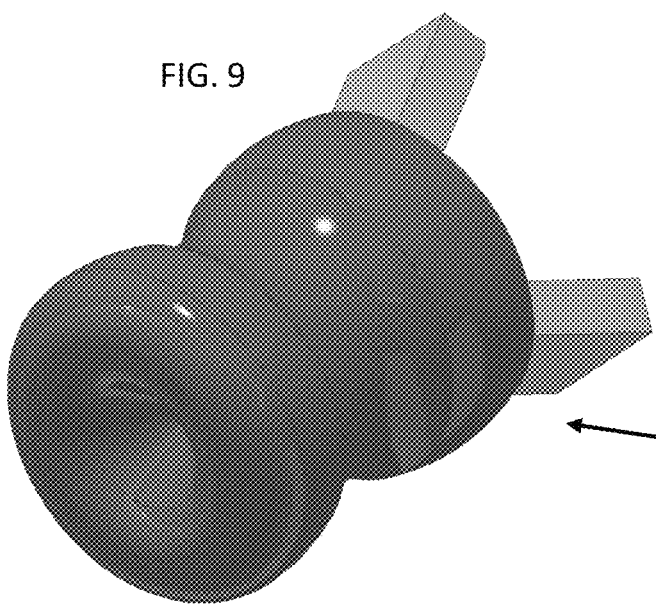
FIG. 9 illustrates an example of an earclip earplug using the earclip support configuration shown in FIG. 7.

FIG. 8 illustrates a cut away 800 of an example of an earclip earplug 810 using the earclip support configuration (system) 700 shown in FIG. 7. The earplug can be composed of a foam or deformable polymer that is deformable when the support configuration 700 is actuated. The foam or deformable polymer can act as the resilient member to provide a restoring force to place the earplug 800 and 900 into a pre insertion state. FIG. 9 illustrates an example of an earclip earplug 900 using the earclip support configuration shown in FIG. 7. Note that a curved (recess) midsection 910 can optionally be included, so that when the earclip support system 700 is actuated the deformed material can partially move into the curved or recess section 910.

FIG. 10 illustrates an example of an earclip support configuration/system 1100, with a tip system 1030 included. The tip system 1030 can be composed of a flexible material such as one of ordinary skill of fabricating eartips, for example polymers and foam.

FIG. 11 illustrates an example of an earclip system 1100 in the insertion configuration. While FIG. 12 illustrates an example of an earclip configuration in a normal orientation 1200. FIG. 13 illustrates an example of an earclip configuration in a normal orientation 1300 with a retention system 1310. The retention (resilient) system (member) 1310 can be deformed providing a restoring force when the earclip system is actuated (e.g., squeezed at one end, AA). FIG. 14 illustrates an example of an earclip configuration in an insertion orientation 1400. Where the resilient member 1310 is deformed 1410 which will force the earclip structure open when not actuated (AA).

Figure 15:
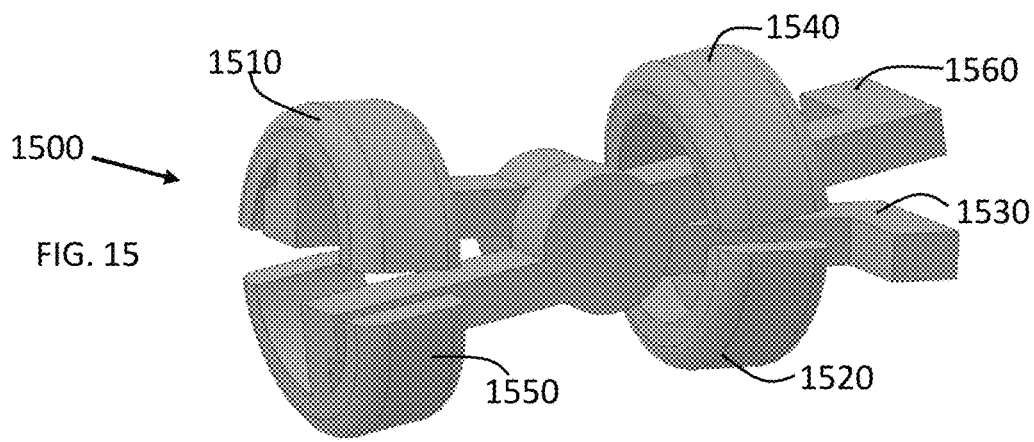
FIG. 15 illustrates an example of an earclip support configuration, with a contact system included.

FIG. 15 illustrates an example of an earclip support configuration 1500, which includes a first arm 1560, a second arm 1530, connected by a pivot 1570, with a contact system 1510, 1520, 1540, and 1550 included. The contact system can be composed of any form of eartip material (e.g., foam, polymer, silicone), an inflatable system (e.g., a urethane balloon, membrane, silicone), or other systems known by one of ordinary skill in the fabrication of ear tip systems.

Figure 16:
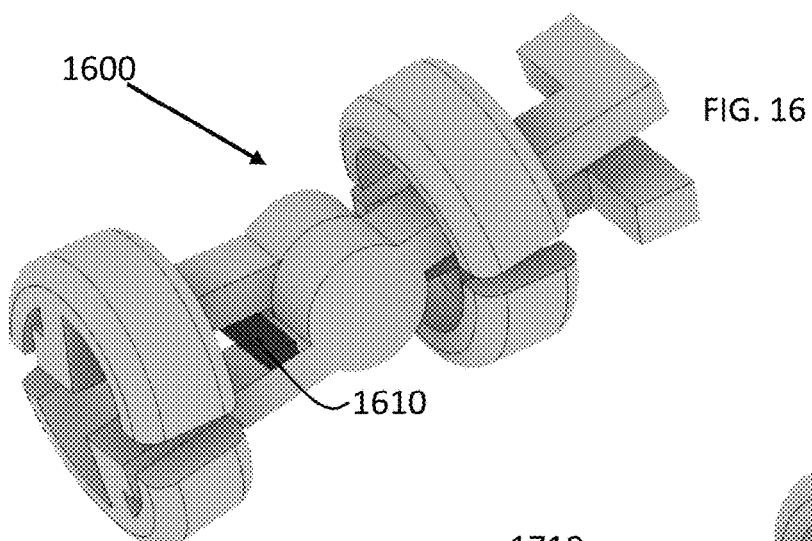
FIG. 16 illustrates an example of an earclip configuration in a normal orientation with a retention system.
Figure 17:
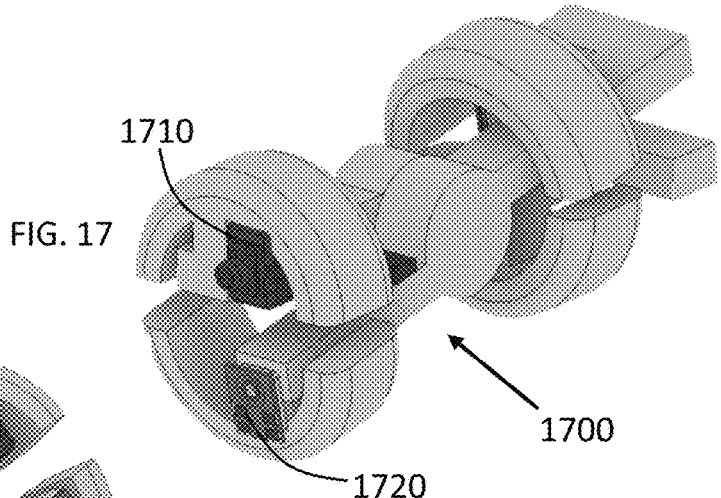
FIG. 17 illustrates an example of an earclip earphone configuration in a normal orientation with a retention system.
Figure 18:
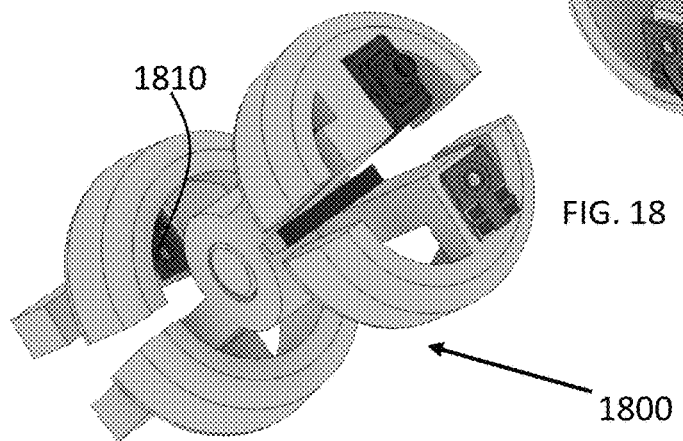
FIG. 18 illustrates an example of an earclip earphone configuration in a normal orientation with a retention system.

FIG. 16 illustrates an example of the earclip configuration 1500 in a normal orientation 1600 with a retention system 1610. FIG. 17 illustrates an example of an earclip earphone 1700 configuration in a normal orientation 1600 with a retention system 1610. The earclip earphone 1700 can include a first microphone 1720, a speaker 1710, and can include a second microphone 1810. FIG. 18 illustrates the earclip earphone 1800 from a different angle to view the second microphone 1810.

FIG. 19 illustrates an example of an earphone 1900 configured to accept sealing elements. The earphone 1900 includes a housing 1930, a stent 1910, a distal end 1925, a sealing/contact element key 1920, a grasping element 1960, a microphone port 1950, and an interaction or visual element 1940.

FIG. 20 illustrates an example of an earphone 1900 configuration of FIG. 19 from another view showing the earphone 2000 includes two sealing/contact element keys 2030 and 2040, a speaker port 2020, and a second microphone port 2010.

FIG. 21 illustrates an example of an cross sectional cut 2100 of the earphone configuration of FIG. 19 from a first view, illustrating in more detail an ambient sound microphone 2110 which samples the local ambient environment via an ambient microphone port 2120.

FIG. 22 illustrates an example of an cross sectional cut 2200 of the earphone configuration of FIG. 19 from a second view, illustrating in more detail an ambient sound microphone 2240, speaker 2210, the sound port 2230 which transmits sound from the speaker to the distal end of the earphone, an ear canal microphone 2220 with associated port 2250.

Figure 23:
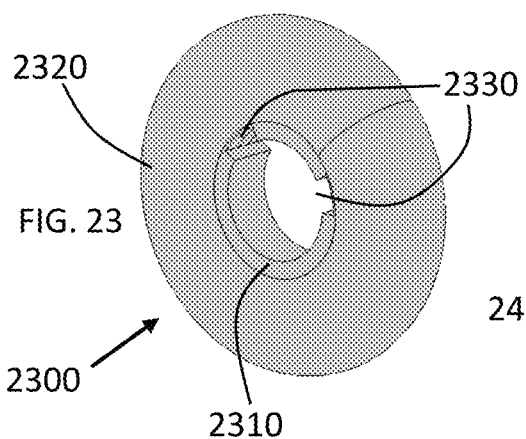
FIG. 23 illustrates an example of a swappable contact system.
Figure 24:
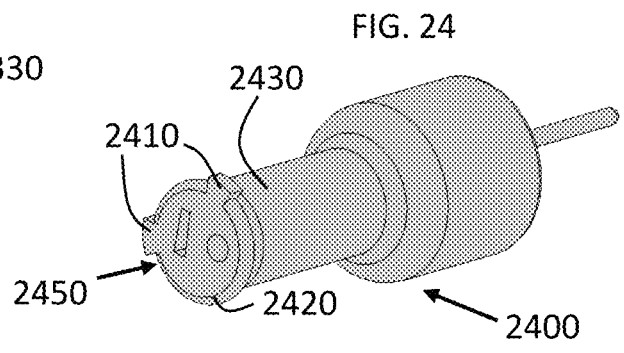
FIG. 24 illustrates an example of an earphone configuration.

FIG. 23 illustrates an example of a swappable contact or sealing system 2300 with a contact region 2320, which includes keys 2330 on a rim 2310 that match keys 2410 on an earphone's (FIG. 24, 2400) stent's (FIG. 24, 2430) distal end (FIG. 24, 2450) lip/ridge (FIG. 24, 2420).

Figure 25:
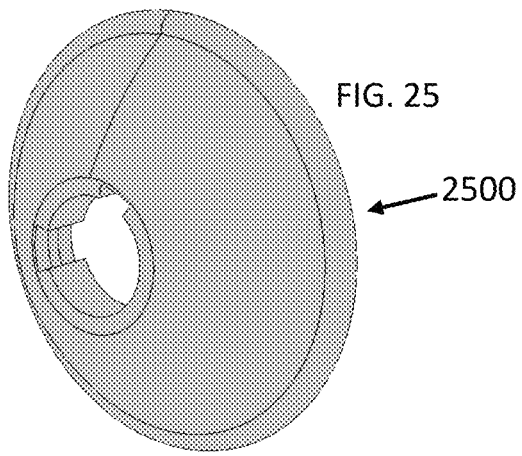
FIG. 25 illustrates an example of a swappable contact system.
Figure 26:
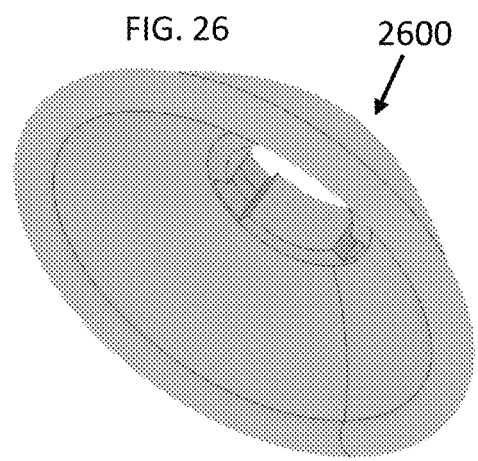
FIG. 26 illustrates an example of a swappable contact system.

FIGS. 25 and 26 illustrate two views (2500, 2600) of a flange example of a swappable contact system 2500.

Figure 27:
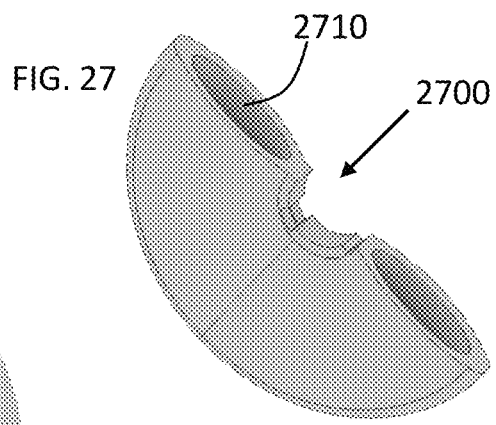
FIG. 27 illustrates an example of a cross section of a swappable contact system.

FIG. 27 illustrates an example of a cross section of a swappable contact system 2700 having a sealed cross section 2710.

Figure 28:
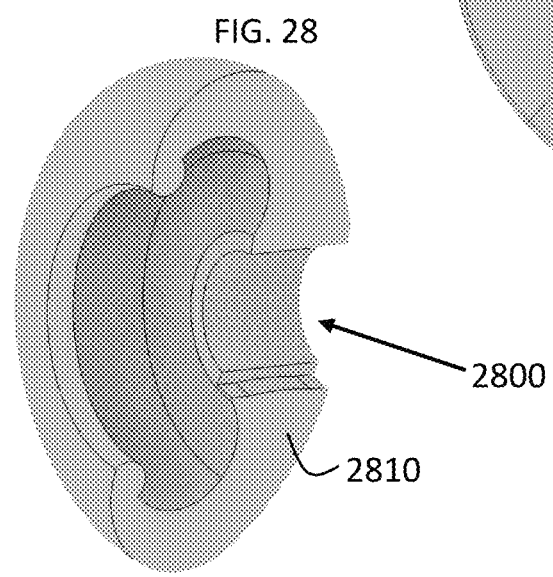
FIG. 28 illustrates an example of a cross section of a swappable contact system.
Figure 29:
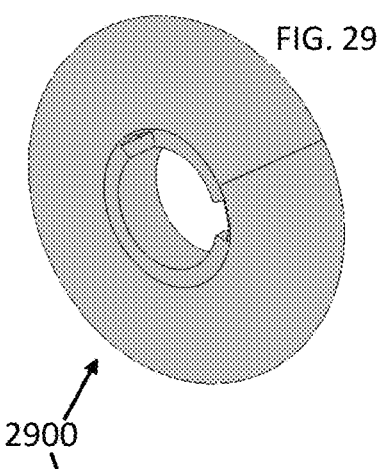
FIGS. 29-30 illustrates an example of placing a contact system onto an adjustable earphone stent.
Figure 30:
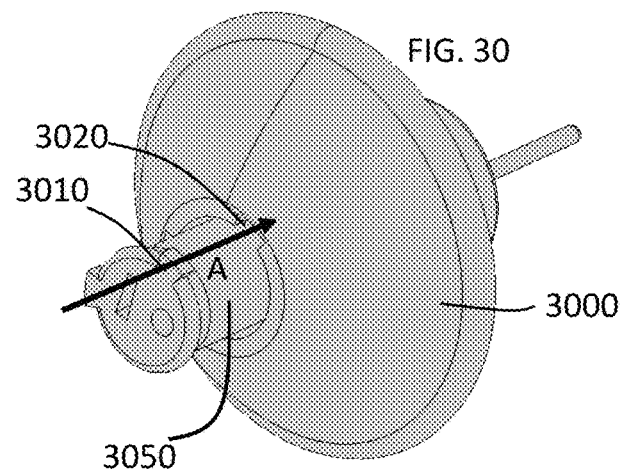
Figure 31:
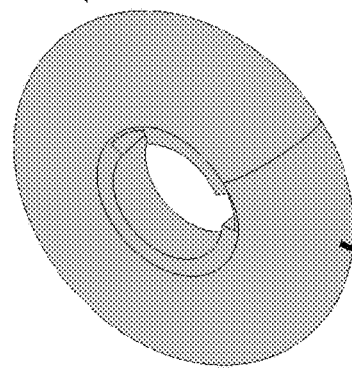
FIGS. 31-32 illustrates an example of placing a contact system onto an adjustable earphone stent.
Figure 32:
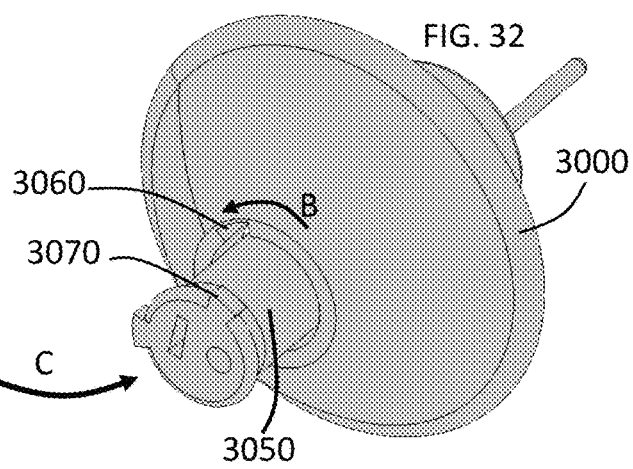

FIG. 28 illustrates another example of a cross section 2800 of a swappable contact system have an open cross section 2810.

FIGS. 29-32 illustrates an example of placing a contact system 2900 onto (C) an adjustable earphone's stent 3050. A previous contact system was slid (A) by lining the keys and moving (A) the contact system 3000 axially from 3010 to 3020. The contact system 3000 can then be rotated (B) to unalign the contact system keys 3060 from the keys 3070 on the stent 3050. Note if the stent keys 3070 are not symmetrically placed circumferentially the likelihood of the contact keys 3060 realigning is remote.

Figure 33:
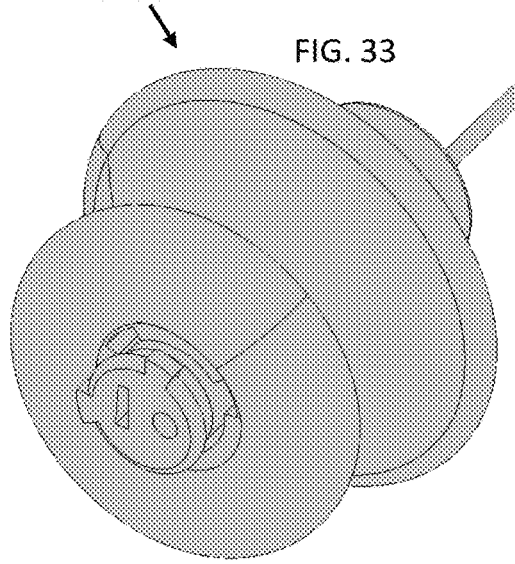
FIGS. 33-34 illustrates an example of placing a contact system onto an adjustable earphone stent.
Figure 34:
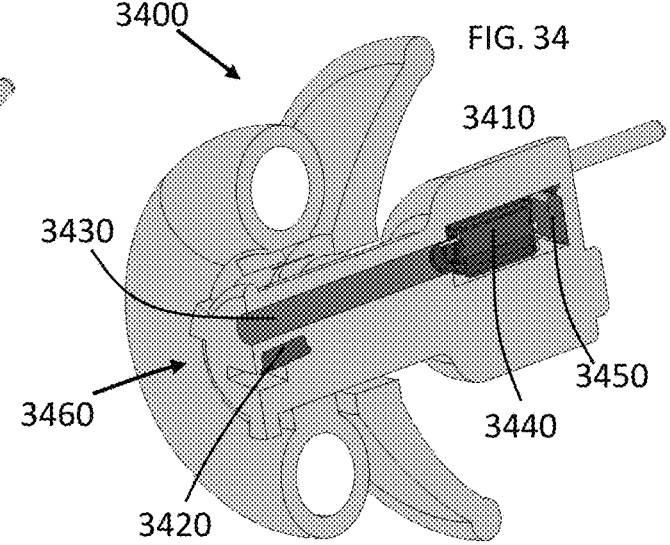

FIG. 33 illustrates an example of an earphone 3300 with the contact elements attached. FIG. 34 illustrates a cross section of the earphone of FIG. 33, including an ambient sound microphone 3450, a speaker 3440, an acoustic tube 3430 to direct the acoustic energy of the speaker 3440 toward the distal end 3460 of the earphone 3410 and an optional ear canal microphone 3420.

Note that a speaker and microphone can be of various types, for example a transducer, a bone conduction speaker and microphone, or any other type of microphone or speaker that can be used in an earphone as known by one of ordinary skill in the art of earphone design.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

Exemplary embodiments can include logic circuits/processors. The logic circuits/processors can utilize microprocessor and/or digital signal processor (DSP) with associated storage memory such a Flash, ROM, RAM, SRAM, DRAM or other like technologies for controlling operations of the aforementioned components (e.g., microphone, speaker) of the earclip device.

What is claimed is:

1. An ear canal insertion device comprising:
    an earclip support, wherein the earclip support includes:
        a first arm;
        a second arm, wherein the first arm and the second arm pivot about a common pivot point forming an angle;
        a resilient member, wherein the resilient member is positioned between the first arm and second arm, wherein the resilient member is configured to rotate the first arm and the second arm about the common pivot point to a first angle of an unactuated position, wherein the earclip support is actuated when a second angle between the first arm and the second arm is less than the first angle; and
    a first and a second contact system, wherein the first contact system is connected to the first arm and the second contact system is connected to the second arm, where the ear canal insertion device is configured to insert at least a portion of the first and second contact system past the aperture of an ear canal when the earclip support is actuated and inserted.

2. The device according to claim 1, where the first and second contact system are combined into a foam earplug.

3. The device according to claim 1, where the resilient member is attached between a portion of the first arm and a second portion of the second arm.

4. The device according to claim 3, where the first contact system is in the form of a first half tip.

5. The device according to claim 4, where the second contact system is in the form of a second half tip.

6. The device according to claim 5, where the first and second half tips are made of a polymer.

7. The device according to claim 5, where the first and second half tips are made of foam.

8. The device according to claim 3, further including a first microphone.

9. The device according to claim 8, further including a speaker.

10. The device according to claim 9, further including a second microphone.

11. The device according to claim 10, where the second microphone is located closer to a distal end of the device than the first microphone.

12. The device according to claim 11 further including a processor.

13. An ear canal insertion device comprising:
    an earclip support, wherein the earclip support includes:
        a first arm;
        a second arm, wherein the first arm and the second arm pivot about a common pivot point forming an angle;
        a resilient member, wherein the resilient member is positioned between the first arm and second arm, wherein the resilient member is configured to rotate the first arm and the second arm about the pivot point to a first angle of an unactuated position, wherein the earclip support is actuated when a second angle between the first arm and the second arm is less than the first angle; and
    a first and a second contact system, wherein the first contact system is connected to the first arm and the second contact system is connected to the second arm, wherein the first contact system includes two portions, a first portion and a second portion, where the first and second portions are on opposite sides of the common pivot point, where the ear canal insertion device is configured to insert at least a portion of the device past the aperture of an ear canal.

14. The device according to claim 13, where the first and second portion are made of foam.

15. The device according to claim 13, where the first and second portion are made of polymer.

16. An ear canal insertion device comprising:
an earclip support, wherein the earclip support includes:
   a first arm;
   a second arm, wherein the first arm and the second arm pivot about a common pivot point forming an angle;
   a resilient member, wherein the resilient member is positioned between the first arm and second arm, wherein the resilient member is configured to rotate the first arm and the second arm about the common pivot point to a first angle of an unactuated position, wherein the earclip support is actuated when a second angle between the first arm and the second arm is less than the first angle;
a first and second contact system, wherein the first contact system is connected to the first arm and the second contact system is connected to the second arm, where the ear canal insertion device is configured to insert at least a portion of the device past the aperture of an ear canal; and
a first microphone.

17. The device according to claim 16, further including a speaker.

18. The device according to claim 17, further including a second microphone.

* * * * *

UNITED STATES PATENT AND TRADEMARK OFFICE
CERTIFICATE OF CORRECTION

| | |
|---|---|
| PATENT NO. | : 11,291,456 B2 |
| APPLICATION NO. | : 16/851896 |
| DATED | : April 5, 2022 |
| INVENTOR(S) | : John P. Keady and Steven W. Goldstein |

It is certified that error appears in the above-identified patent and that said Letters Patent is hereby corrected as shown below:

On the Title Page

Item (12) "Keady" should read --Keady et al.--

Item (72) Inventor should read:
--(72) Inventors: John P. Keady, Fairfax Station, VA (US);
Steven W. Goldstein, Delray Beach, FL (US)--

Signed and Sealed this
Sixteenth Day of July, 2024

Katherine Kelly Vidal
*Director of the United States Patent and Trademark Office*